(12) United States Patent
Xing et al.

(10) Patent No.: US 9,704,154 B2
(45) Date of Patent: Jul. 11, 2017

(54) WEARABLE PERSONAL DIGITAL DEVICE FOR FACILITATING MOBILE DEVICE PAYMENTS AND PERSONAL USE

(71) Applicants: Zhou Tian Xing, Tiburon, CA (US); Dylan T X Zhou, Belvedere Tiburon, CA (US); Tiger T G Zhou, Tiburon, CA (US); Andrew H B Zhou, Tiburon, CA (US)

(72) Inventors: Zhou Tian Xing, Tiburon, CA (US); Dylan T X Zhou, Belvedere Tiburon, CA (US); Tiger T G Zhou, Tiburon, CA (US); Andrew H B Zhou, Tiburon, CA (US)

(73) Assignee: WORLD AWARD ACADEMY, WORLD AWARD FOUNDATION, AMOBILEPAY, INC., Austin, TX (US)

( * ) Notice: Subject to any disclaimer, the term of this patent is extended or adjusted under 35 U.S.C. 154(b) by 0 days.

(21) Appl. No.: 15/439,276

(22) Filed: Feb. 22, 2017

(65) Prior Publication Data
US 2017/0161720 A1 Jun. 8, 2017

Related U.S. Application Data

(63) Continuation-in-part of application No. 15/343,227, filed on Nov. 4, 2016, and a continuation-in-part of
(Continued)

(51) Int. Cl.
*G06Q 20/32* (2012.01)
*A61B 5/00* (2006.01)
(Continued)

(52) U.S. Cl.
CPC ....... *G06Q 20/3278* (2013.01); *A61B 5/0024* (2013.01); *A61B 5/02007* (2013.01);
(Continued)

(58) Field of Classification Search
CPC ..... G06F 21/6245; G06F 21/32; A61B 5/681; A61B 5/0024; A61B 5/1117; A61B 10/0051; G06K 19/06112
See application file for complete search history.

(56) References Cited

U.S. PATENT DOCUMENTS 8,784,271 B2 * 7/2014 Brumback ............... 340/870.16
9,100,493 B1 * 8/2015 Zhou ................ H04M 1/72522
(Continued)

OTHER PUBLICATIONS

New Biosenseor Detects microRNA Biomarkers for Cancer. http://bostoncommons.net/new-biosensor-detects-microrna-biomakers-for-cancer/ Mar. 13, 2016 by BCNet Staff.*

*Primary Examiner* — Daniel Walsh
(74) *Attorney, Agent, or Firm* — Georgiy L. Khayet

(57) ABSTRACT

Provided are a wearable personal digital device and related methods. The wearable personal digital device may comprise a processor, a display, biometric sensors, activity tracking sensors, a memory unit, a communication circuit, a housing, an input unit, a projector, a timepiece unit, a haptic touch control actuator, and a band. The processor may be operable to receive data from an external device, provide a notification to a user based on the data, receive a user input, and perform a command selected based on the user input. The communication circuit may be communicatively coupled to the processor and operable to connect to a wireless network and communicate with the external device. The housing may be adapted to enclose the components of the wearable personal digital device. The band may be adapted to attach to the housing and secure the wearable personal digital device on a user body.

23 Claims, 9 Drawing Sheets

Related U.S. Application Data application No. 15/345,349, filed on Nov. 7, 2016, now Pat. No. 9,652,758, which is a continuation-in-part of application No. 14/957,644, filed on Dec. 3, 2015, now Pat. No. 9,489,671, which is a continuation-in-part of application No. 14/815,988, filed on Aug. 1, 2015, now Pat. No. 9,342,829, which is a continuation-in-part of application No. 13/760,214, filed on Feb. 6, 2013, now Pat. No. 9,016,565, which is a continuation-in-part of application No. 10/677,098, filed on Sep. 30, 2003, now Pat. No. 7,702,739, said application No. 15/439,276 is a continuation-in-part of application No. 14/695,256, filed on Apr. 24, 2015, now Pat. No. 9,100,493.

(60) Provisional application No. 60/415,546, filed on Oct. 1, 2002.

(51) Int. Cl.

| | | |
|---|---|---|
| *G06F 21/32* | (2013.01) | |
| *G06Q 20/40* | (2012.01) | |
| *G06F 21/62* | (2013.01) | |
| *G06F 3/16* | (2006.01) | |
| *G10L 15/22* | (2006.01) | |
| *G10L 15/18* | (2013.01) | |
| *G06F 3/0488* | (2013.01) | |
| *G10L 21/0208* | (2013.01) | |
| *G06F 3/041* | (2006.01) | |
| *A61B 5/0205* | (2006.01) | |
| *A61B 5/0402* | (2006.01) | |
| *A61B 5/11* | (2006.01) | |
| *A61B 5/1172* | (2016.01) | |
| *A61B 5/145* | (2006.01) | |
| *A61B 10/00* | (2006.01) | |
| *A61B 5/02* | (2006.01) | |
| *G06K 9/00* | (2006.01) | |
| *G06K 7/14* | (2006.01) | |
| *G06K 7/10* | (2006.01) | |
| *A61B 5/01* | (2006.01) | |
| *A61B 5/024* | (2006.01) | |
| *A61B 5/08* | (2006.01) | |
| *A61B 5/021* | (2006.01) | |

(52) U.S. Cl.
CPC ........ *A61B 5/02055* (2013.01); *A61B 5/0402* (2013.01); *A61B 5/112* (2013.01); *A61B 5/1112* (2013.01); *A61B 5/1117* (2013.01); *A61B 5/1118* (2013.01); *A61B 5/1172* (2013.01); *A61B 5/14507* (2013.01); *A61B 5/14532* (2013.01); *A61B 5/14546* (2013.01); *A61B 5/4818* (2013.01); *A61B 5/4848* (2013.01); *A61B 5/4866* (2013.01); *A61B 5/681* (2013.01); *A61B 5/6804* (2013.01); *A61B 5/7405* (2013.01); *A61B 5/746* (2013.01); *A61B 5/7425* (2013.01); *A61B 5/7455* (2013.01); *A61B 5/7495* (2013.01); *A61B 10/0051* (2013.01); *G06F 3/0414* (2013.01); *G06F 3/04883* (2013.01); *G06F 3/04886* (2013.01); *G06F 3/167* (2013.01); *G06F 21/6245* (2013.01); *G06Q 20/3276* (2013.01); *G06Q 20/40145* (2013.01); *G10L 15/18* (2013.01); *G10L 15/22* (2013.01); *G10L 21/0208* (2013.01); *A61B 5/015* (2013.01); *A61B 5/021* (2013.01); *A61B 5/02433* (2013.01); *A61B 5/0816* (2013.01); *A61B 2560/0252* (2013.01); *A61B 2562/028* (2013.01); *A61B 2562/0219* (2013.01); *G06K 7/1404* (2013.01); *G06K 9/00087* (2013.01); *G06K 9/00892* (2013.01); *G06K 2007/10534* (2013.01); *G06K 2009/00939* (2013.01); *G06K 2209/01* (2013.01); *G10L 2015/223* (2013.01)

(56) References Cited

U.S. PATENT DOCUMENTS

| | | | | |
|---|---|---|---|---|
| 9,299,238 | B1* | 3/2016 | Ahmad | A61B 5/4833 |
| 2002/0055117 | A1* | 5/2002 | Fett | C12Q 1/6886 |
| | | | | 435/6.14 |
| 2003/0165954 | A1* | 9/2003 | Katagiri | C12Q 1/6883 |
| | | | | 435/6.14 |
| 2003/0175993 | A1* | 9/2003 | Toranto | G01N 33/487 |
| | | | | 436/518 |
| 2006/0057707 | A1* | 3/2006 | Cunningham | B01L 3/5085 |
| | | | | 435/287.1 |
| 2008/0022089 | A1* | 1/2008 | Leedom | H04L 63/068 |
| | | | | 713/156 |
| 2008/0038738 | A1* | 2/2008 | Weigum | A61B 5/0059 |
| | | | | 435/6.12 |
| 2008/0266546 | A1* | 10/2008 | Kolesnychenko | G01N 21/0303 |
| | | | | 356/51 |
| 2013/0146659 | A1* | 6/2013 | Zhou | G06Q 20/355 |
| | | | | 235/380 |
| 2013/0231711 | A1* | 9/2013 | Kaib | G06F 19/3418 |
| | | | | 607/5 |
| 2013/0234850 | A1* | 9/2013 | Lee | A61B 5/02 |
| | | | | 340/539.12 |
| 2013/0346168 | A1* | 12/2013 | Zhou | G06F 1/163 |
| | | | | 705/14.4 |
| 2014/0139422 | A1* | 5/2014 | Mistry | G06F 3/014 |
| | | | | 345/156 |
| 2014/0139486 | A1* | 5/2014 | Mistry | G06F 3/0304 |
| | | | | 345/175 |
| 2014/0139637 | A1* | 5/2014 | Mistry | H04N 5/2252 |
| | | | | 348/46 |
| 2014/0143737 | A1* | 5/2014 | Mistry | G06F 3/0488 |
| | | | | 715/854 |
| 2014/0180595 | A1* | 6/2014 | Brumback | A61B 5/0015 |
| | | | | 702/19 |
| 2014/0239065 | A1* | 8/2014 | Zhou | G06F 1/163 |
| | | | | 235/380 |
| 2014/0275850 | A1* | 9/2014 | Venkatraman | A61B 5/0002 |
| | | | | 600/301 |
| 2014/0275852 | A1* | 9/2014 | Hong | A61B 5/02427 |
| | | | | 600/301 |
| 2014/0275854 | A1* | 9/2014 | Venkatraman | A61B 5/721 |
| | | | | 600/301 |
| 2014/0276244 | A1* | 9/2014 | Kamyar | A61B 5/1112 |
| | | | | 600/595 |
| 2014/0316305 | A1* | 10/2014 | Venkatraman | A61B 5/1112 |
| | | | | 600/595 |
| 2014/0366123 | A1* | 12/2014 | DiBona | G06Q 10/00 |
| | | | | 726/16 |
| 2015/0073907 | A1* | 3/2015 | Purves | G06Q 20/32 |
| | | | | 705/14.58 |
| 2015/0186609 | A1* | 7/2015 | Utter, II | A61B 5/0022 |
| | | | | 600/301 |
| 2015/0196200 | A1* | 7/2015 | Fixler | A61B 5/02007 |
| | | | | 600/431 |
| 2015/0238150 | A1* | 8/2015 | Subramaniam | H04Q 9/00 |
| | | | | 340/539.11 |
| 2015/0366518 | A1* | 12/2015 | Sampson | A61B 5/7221 |
| | | | | 600/301 |
| 2015/0371215 | A1* | 12/2015 | Zhou | G06Q 30/02 |
| | | | | 705/71 |
| 2016/0036811 | A1* | 2/2016 | Shim | G06F 21/6245 |
| | | | | 726/7 |
| 2016/0037346 | A1* | 2/2016 | Boettcher | H04M 1/72519 |
| | | | | 455/411 |
| 2016/0125600 | A1* | 5/2016 | Lee | G01N 21/8483 |
| | | | | 382/128 |

(56) References Cited

U.S. PATENT DOCUMENTS

| | | | | |
|---|---|---|---|---|
| 2016/0162873 A1* | 6/2016 | Zhou | .................. | G06Q 20/3227 |
| | | | | 705/67 |
| 2016/0239624 A1* | 8/2016 | Short | ...................... | G06F 19/18 |
| 2016/0286210 A1* | 9/2016 | Border | ................ | G02B 27/0176 |
| 2016/0328282 A1* | 11/2016 | Rogati | ................ | G06F 11/0772 |
| 2016/0374588 A1* | 12/2016 | Shariff | ................ | A61B 5/7475 |
| | | | | 600/547 |
| 2016/0379205 A1* | 12/2016 | Margadoudakis | ... | G06Q 20/327 |
| | | | | 705/71 |
| 2017/0011210 A1* | 1/2017 | Cheong | ................ | H04W 12/06 |
| 2017/0011223 A1* | 1/2017 | Dang | .................... | G06F 21/606 |
| 2017/0018150 A1* | 1/2017 | Kim | ........................ | G07C 9/00 |
| 2017/0031449 A1* | 2/2017 | Karsten | ................ | G06F 19/322 |
| 2017/0039358 A1* | 2/2017 | Yuen | ....................... | G06F 3/017 |
| 2017/0071483 A1* | 3/2017 | Wang | ................ | A61B 5/14551 |

\* cited by examiner

WEARABLE PERSONAL DIGITAL DEVICE FOR FACILITATING MOBILE DEVICE PAYMENTS AND PERSONAL USE

CROSS-REFERENCE TO RELATED APPLICATIONS

This application is a continuation-in-part of U.S. patent application Ser. No. 14/695,256, entitled "WEARABLE PERSONAL DIGITAL DEVICE FOR FACILITATING MOBILE DEVICE PAYMENTS AND PERSONAL USE", filed on Apr. 24, 2015, U.S. patent application Ser. No. 15/343,227, entitled "SYSTEMS AND METHODS FOR MOBILE APPLICATION, WEARABLE APPLICATION, TRANSACTIONAL MESSAGING, CALLING, DIGITAL MULTIMEDIA CAPTURE AND PAYMENT TRANSACTIONS", filed on Nov. 4, 2016, U.S. patent application Ser. No. 15/345,349, entitled "SYSTEMS AND METHODS FOR MESSAGING, CALLING, DIGITAL MULTIMEDIA CAPTURE AND PAYMENT TRANSACTIONS", filed on Nov. 7, 2016; which is a continuation-in-part of U.S. patent application Ser. No. 14/957,644, entitled "SYSTEMS AND METHODS FOR MOBILE APPLICATION, WEARABLE APPLICATION, TRANSACTIONAL MESSAGING, CALLING, DIGITAL MULTIMEDIA CAPTURE AND PAYMENT TRANSACTIONS", filed on Dec. 3, 2015, which is a continuation-in-part of U.S. patent application Ser. No. 14/815,988, entitled "SYSTEMS AND METHODS FOR MOBILE APPLICATION, WEARABLE APPLICATION, TRANSACTIONAL MESSAGING, CALLING, DIGITAL MULTIMEDIA CAPTURE AND PAYMENT TRANSACTIONS", filed on Aug. 1, 2015, which claims priority to U.S. patent application Ser. No. 13/760,214, entitled "WEARABLE PERSONAL DIGITAL DEVICE FOR FACILITATING MOBILE DEVICE PAYMENTS AND PERSONAL USE", filed on Feb. 6, 2013, which is a continuation-in-part of U.S. patent application Ser. No. 10/677,098, entitled "EFFICIENT TRANSACTIONAL MESSAGING BETWEEN LOOSELY COUPLED CLIENT AND SERVER OVER MULTIPLE INTERMITTENT NETWORKS WITH POLICY BASED ROUTING", filed on Sep. 30, 2003, which claims priority to Provisional Application No. 60/415,546, entitled "DATA PROCESSING SYSTEM", filed on Oct. 1, 2002, which are incorporated herein by reference in their entirety.

FIELD

This application relates generally to personal mobile devices and, more specifically, to wearable personal digital devices for facilitating mobile device payments and personal use.

BACKGROUND

Mobile devices gain growing importance in daily activities of their users with more and more functions being performed by mobile devices. Some of such functions may include mobile communication, mobile payments, health monitoring, and so forth. In addition to that, carrying a mobile phone, a tablet personal computer, or a laptop may not always be comfortable, for example, during physical activity or leisure time. For such purposes, wearable mobile devices, e.g. wristwatch digital devices, may be used. However, use of the wearable mobile devices may be inconvenient because of limited software functionality of such devices.

Furthermore, a wristwatch digital device may be communicatively coupled to a smartphone and display notifications related to smartphone activity, e.g. an incoming call or a message. However, a user may be unable to respond to the notification directly using the wristwatch digital device.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Provided are a wearable personal digital device for facilitating mobile device payments, personal use, and health care and a method for facilitating user interaction with a wearable personal digital device for facilitating mobile device payments, personal use, and health care. The wearable personal digital device for facilitating mobile device payments, personal use, and health care use may comprise a processor, a display, one or more biometric sensors, one or more activity tracking sensors, a memory unit, a communication circuit, a housing, an input unit, and a band. The processor may be operable to receive data from an external device, provide a notification to a user based on the data, receive a user input, and perform a command selected based on the user input. The user input may be received through the display (e.g., a touchscreen) or the input unit communicatively coupled to the processor. The input unit may extend from the housing and be configured to perform one or more of a rotational motion and a linear motion. A thin-film sensor made of nanoparticles and polymers, which when pressed against the skin may create changes in electrical current and light (ECL) that can be captured by a high-quality digital camera of wearable device, which may detect tumors as small as 3 millimeters, hidden up to 2-50 millimeters deep in human body, an electrometric radiation that human body emit when their temperature is above the absolute zero, the thermal infrared (IR) sensor range may extend to cover wavelengths from 800 nanometer to few hundred micrometer to detect Cancer using Temperature Variation and Radiation Analysis (TVRA) via wearable computer device, which has grown tangibly due to many factors, such as life expectancies increase, personal habits and ultraviolet radiation exposures among others. The biometric sensors may be operable to sense one or more biometric parameters of the user which can be provided via the display, stored to the memory unit, transmitted to the external device, and so forth. The one or more activity tracking sensors may be communicatively coupled to the processor. The communication circuit may be communicatively coupled to the processor and operable to connect to a wireless network and communicate with the external device. The housing may be adapted to enclose at least the processor, the display, the one or more biometric sensors, the one or more activity tracking sensors, the memory unit, and the communication circuit. The band may be adapted to attach to the housing and to secure the device on a user body.

In some embodiments, the wearable personal digital device for facilitating mobile device payments, personal use, and health care may further include a camera communicatively coupled to the processor. The camera may be operable to capture a code, the codes including one or more of the following: a linear dimensional code, a two-dimensional code, a snap tag code, and a Quick Response code. The code may be read by the processor to obtain one or more of product information and merchant information encoded in the code, and initiate a payment transaction based on the merchant information.

Furthermore, the display may be operable to be activated based on one or more of the following: a movement of a user hand, a movement of the user body, a gesture performed by the user in proximity to the display, and a user voice. Additionally, the display may display data associated with the activity of the user, such as calories burned, sleep quality, breaths per minute, snoring breaks, steps walked, distance walked, and so forth.

In further exemplary embodiments, modules, subsystems, or devices can be adapted to perform the recited steps. Other features and exemplary embodiments are described below.

BRIEF DESCRIPTION OF DRAWINGS

Embodiments are illustrated by way of example and not limitation in the figures of the accompanying drawings, in which like references indicate similar elements and in which.

DETAILED DESCRIPTION

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting.

A wearable personal digital (WPD) device for facilitating mobile device payments, personal use, and health care and related methods are described herein. The WPD device may include a housing enclosing all components of the WPD device and a band attached to the housing. Furthermore, the WPD device may perform a function of a health and activity monitor. More specifically, the WPD device may sense biometric data associated with the user (blood pressure, heart rate, temperature, and so forth) using biometric sensors and/or receive data on user movements using accelerometers or a Global Positioning System (GPS) unit. Biometric data and user movement data may be shown on a display of the WPD device, stored in a memory unit of the WPD device, and/or processed by a processor of the WPD device to produce historical or averaged data.

The WPD device may be communicatively coupled with an external device, such as a smartphone. The WPD device and the smartphone may communicate using a wireless network, such as a Wi-Fi network or a Bluetooth network. The WPD device may display notifications from the smartphone. The notifications may represent receipt of any type of data by the smartphone, for example, a phone call, a message, an upcoming calendar event, a social network event, and the like. A user may respond to the notification directly via the WPD device, or using the smartphone. The biometric data and user movement data collected by the WPD device may be sent to the smartphone for further processing.

The display of the WPD device may be represented by a touchscreen. The user may provide commands to the WPD device by varying the time of user interaction with the touchscreen. More specifically, the user may vary the time of pressing the touchscreen. Different time of pressing the touchscreen may correspond to different commands. For example, pressing the touchscreen for 1 second may correspond to a message mode. Therefore, after the user touches the touchscreen for 1 sec and releases a user finger from the touchscreen, the message mode may be activated. Similarly, pressing the touchscreen for 5 seconds may correspond to a payment mode. The payment mode may be performed by using scanning of codes. Additionally, payment cards may be read using a swipe card reader optionally included into the WPD device.

Figure 1:
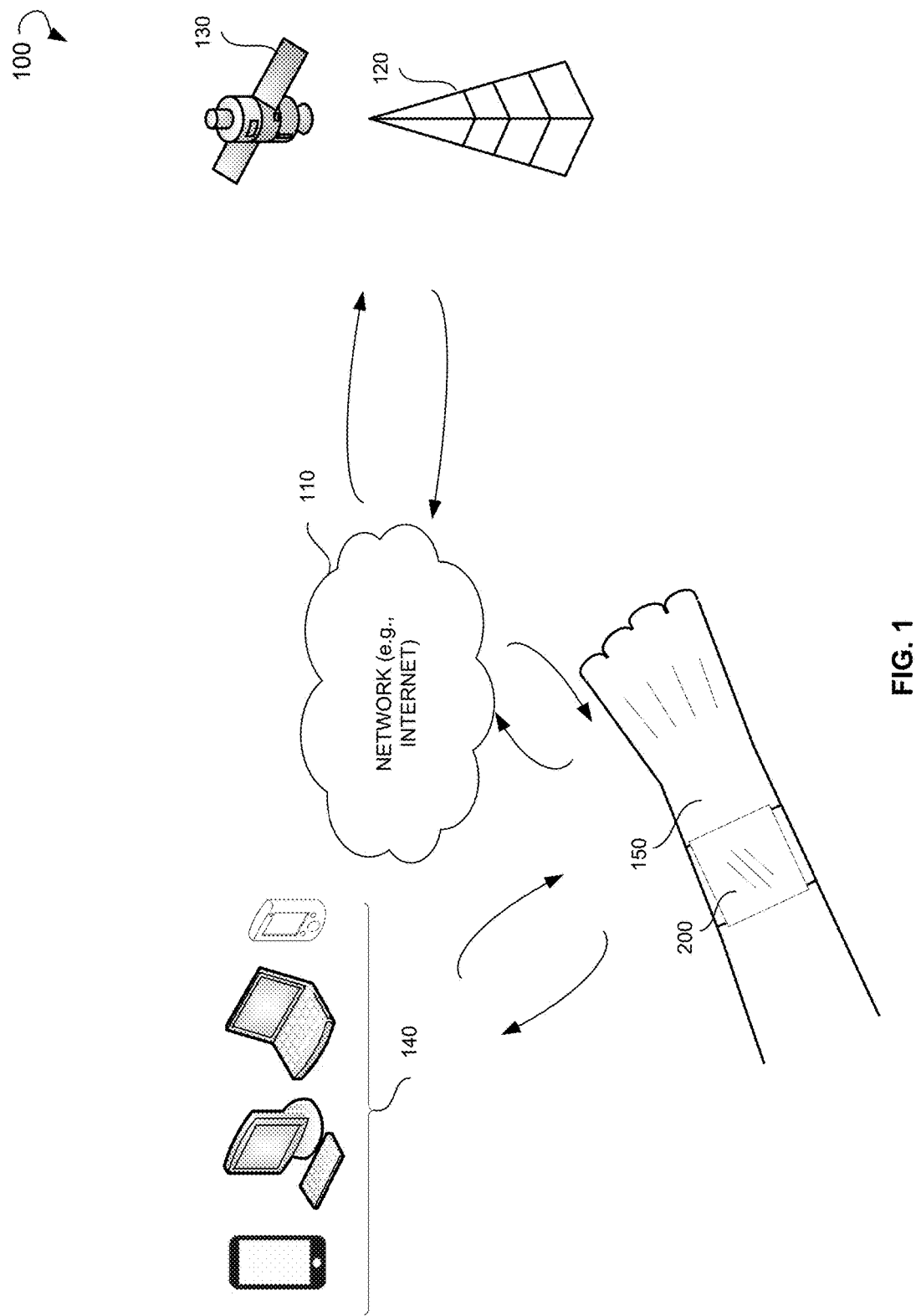
FIG. 1 illustrates an environment within which the wearable personal digital device for facilitating mobile device payments, personal use, and health care and methods for facilitating user interaction with the wearable personal digital device for facilitating mobile device payments and personal use can be implemented, in accordance with some embodiments.

Referring now to the drawings, FIG. 1 illustrates an environment 100 within which the WPD device 200 and methods for facilitating user interaction with the WPD device 200 can be implemented. The environment 100 may include a network 110, a WPD device 200, a mobile base station 120, a GSM satellite 130, and one or more external devices 140. The WPD device 200 may be worn by a user 150. The network 110 may include the Internet or any other network capable of communicating data between devices. Suitable networks may include or interface with any one or more of, for instance, a local intranet, a Personal Area Network, a Local Area Network, a Wide Area Network, a Metropolitan Area Network, a virtual private network, a storage area network, a frame relay connection, an Advanced Intelligent Network connection, a synchronous optical network connection, a digital T1, T3, E1 or E3 line, Digital Data Service connection, Digital Subscriber Line connection, an Ethernet connection, an Integrated Services Digital Network line, a dial-up port such as a V.90, V.34 or V.34bis analog modem connection, a cable modem, an Asynchronous Transfer Mode connection, or an Fiber Distributed Data Interface or Copper Distributed Data Interface connection. Furthermore, communications may also include links to any of a variety of wireless networks, including Wireless Application Protocol, General Packet Radio Service, Global System for Mobile Communication, Code Division Multiple Access or Time Division Multiple Access, cellular phone networks, Global Positioning System, cellular digital packet data, Research in Motion, Limited duplex paging network, Bluetooth radio, or an IEEE 802.11-based radio frequency network. The network 110 can further include or interface with any one or more of an RS-232 serial connection, an IEEE-1394 (Firewire) connection, a Fiber Channel connection, an IrDA (infrared) port, a SCSI (Small Computer Systems Interface) connection, a Universal Serial Bus (USB) connection or other wired or wireless, digital or analog interface or connection, mesh or Digi® networking. The network 110 may be a network of data processing nodes that are interconnected for the purpose of data communication. The WPD device 200 may communicate with the GPS satellite via the network 110 to exchange data on a geographical location of the WPD device 200. Additionally, the WPD device 200 may communicate with mobile network operators using the mobile base station 120.

For the purposes of communication, the WPD device 200 may be compatible with one or more of the following network standards: GSM, CDMA, LTE, IMS, Universal Mobile Telecommunication System (UMTS), 4G, 5G, 6G and upper, RFID, and so forth.

Figure 2:
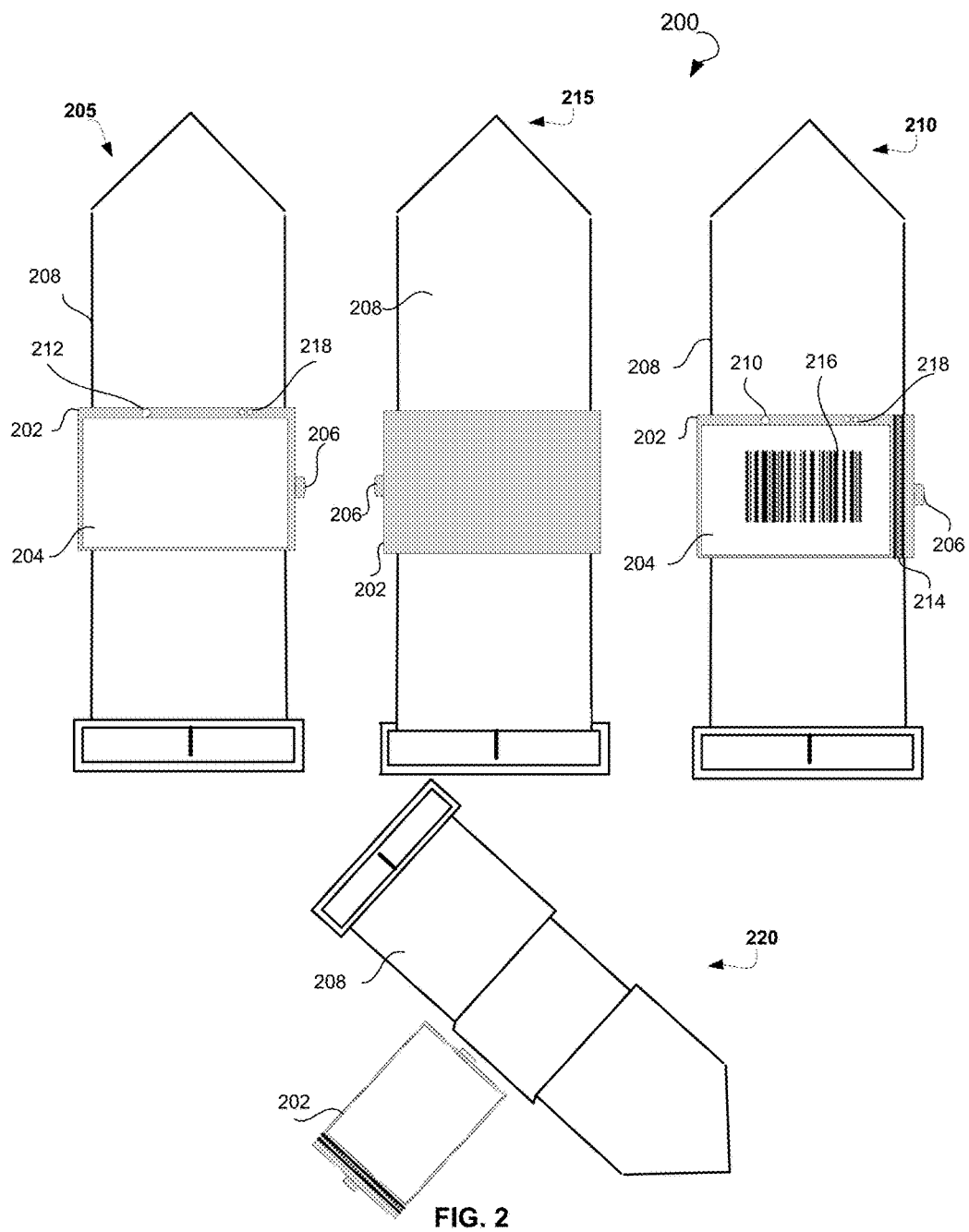
FIG. 2 illustrates an example wearable personal digital device for facilitating mobile device payments, personal use, and health care, in accordance with some embodiments.

FIG. 2 illustrates an example of the WPD device 200 in accordance with some embodiments. FIG. 2 shows a front view 205 of the WPD device 200 according to one example embodiment, a front view 210 of the WPD device 200 according to another example embodiment, a back view 215 of the WPD device 200 according to an example embodiment, and a detached view 220 of the WPD device 200 according to an example embodiment.

As shown on the front view 205 and the back view 215 of FIG. 2, the WPD device 200 may comprise a housing 202, which encloses a processor (not shown), a display 204, a memory unit (not shown) communicatively coupled to the processor, a communication circuit (not shown), biometric sensors (not shown) operable to sense one or more biometric parameters of the user, activity tracking sensors (not shown), an input unit 206, a projector (not shown), a timepiece unit (not shown), a haptic touch control actuator (not shown), a near field communication (NFC) unit (not shown) communicatively coupled to the processor, and a band 208.

The processor may be operable to receive data from an external device (not shown). Based on the data, the processor may be operable to provide a notification to a user. In an example embodiment, the notification may be provided via one or more of the following: a vibration, a sound, a light indication, and so forth. The light indication may be generated using a light indicator 218. The processor may be further operable to receive a user input provided by the user in response to reviewing the notification. Furthermore, the processor may be operable to perform a command selected based on the user input. The processor may be further operable to provide a natural language user interface to communicate with the user. The natural language user interface may be operable to sense a user voice and provide a response in a natural language to the user. The WPD device 200 may further include an operating system being executed on the processor. The operating system may include Android, iOS, Firefox OS, and so forth.

The display 204 may be communicatively coupled to the processor. In an example embodiment, the display 204 includes a touchscreen. The display 204 may be used to receive the user input. More specifically, the user may provide the user input by pressing the display 204, performing movements on the display 204 (e.g. moving a finger from left to right, from up to down, and the like). In an example embodiment, the display 204 includes a force sensor. The force sensor may be operable to sense a touch force applied by the user to the display 204 and calculate coordinates of a touch by the user. The force sensor may be further operable to analyze the touch force and, based on the touch force, select a tap command or a press command based on a predetermined criteria. The predetermined criteria may include a value of the touch force. In an example embodiment, the display 204 may be operable to be activated based on one or more of the following: a movement of a user hand, a movement of the user body, a gesture performed by the user in proximity to the display, a user voice, and so forth.

In a further example embodiment, the processor may be operable to detect absence of interaction of the user with the display. The detection may be made based on an eye tracking of the user, a head tracking of the user, and a spatial position of the housing. Based on the detecting, the processor may be operable to dim the display 204. Additionally, the processor may be operable to activate the display 204 based on a spatial position of the housing or a gesture of the user body, such as a user hand.

In a further example embodiment, the processor may be operable to receive, using the natural language user interface, a map request from the user. In response to the map request, the processor may display via the display 204, a map and a route depicted on the map. Additionally, the processor may be operable to provide an indication associated with the route to the user. The indication may be provided using the haptic feedback. The indication may include for example, providing haptic feedback, such as a vibration, one time for a direction to the left, two times for the direction to the right, or any other type of feedback.

In a further example embodiment, the processor may be operable to analyze a message received by the external device. The analyzing may include one or more of the following: parsing a text; reading an image, recognizing a voice, and the like. Based on the analysis, one or more possible replies may be displayed to the user using the display 204. Furthermore, a selection of a reply from the one or more possible replies may be received from the user. Based on the selection, the processor may be operable to send the reply to the external device.

In an example embodiment, the processor may be operable to analyze the user activity. Based on the analyzing, one or more diagrams may be displayed to the user. The one or mode diagrams may represent one or more activity types of the user.

The projector may be communicatively coupled to the processor. The projector may be operable to project a data onto a viewing surface. The data may include one or more of the following: a virtual keyboard, the notification of the external device, time, data requested by the user, a caller name, a text message, a reminder, a social media alert, an email, a weather alert, and the like. The viewing surface may include a user arm, a user hand, and any surface in proximity to the WPD device 200. In an example embodiment, the projector may project data to the left side or to the right side with respect to the wrist of the user.

The timepiece unit may be communicatively coupled to the processor and configured to provide time data.

The communication circuit may be communicatively coupled to the processor and configured to connect to a wireless network and communicate with the external device. In an example embodiment, the communication circuit may include one or more of the following: a wireless transceiver, a Bluetooth module, a Wi-Fi module, a communication port, and the like. The communication port may include one or more of the following: a USB port, a parallel port, an infrared transceiver port, a radiofrequency transceiver port, and so forth.

The input unit 206 may be communicatively coupled to the processor. In an example embodiment, the input unit 206 may extend from the housing 202 and may be configured to perform a rotational motion and a linear motion. Therefore, the input unit 206 may be rotated around a longitudinal axis of the input unit 206, may be pushed into the housing 202, or may be extended from the housing 202. Thus, the input unit 206 may be operable to receive the user input.

The band 208 may be adapted to attach to the housing 202 and to secure the WPD device 200 on a user body or clothes of the user. In various embodiments, the WPD device 200 may be secured on a wrist, an arm, a neck, a head, a leg, a waist, an ear, a finger, or any other part of the human body, or on any part of the clothes of the user. The band 208 may be adapted to secure the WPD device 200 under, within or on the clothes of the user. The band 208 may be an expansion bracelet, one piece band, two piece band, and so forth. In some embodiments, the band 208 may include a clasp adapted to fix the band 208 in a specific position to secure the WPD device 200 around the wrist.

In an example embodiment, the WPD device 200 may further include a camera 212. The camera 212 may be configured to capture a code, such as a linear dimensional code, a two-dimensional code, a snap tag code, and a Quick Response (QR) code. Upon capturing the code by the camera 212, the processor may be operable to read the captured code to obtain product information or merchant information encoded in the code. More specifically, the user may capture barcodes of products provided in a store. Upon reading the barcode, product information may be provided to the user on the display 204. In an example embodiment, the product information may be displayed on the external device, such as a smartphone. Additionally, the merchant information may be retrieved from the barcode. The merchant information may include merchant payment information. Upon obtaining product information and merchant information, the processor may initiate a payment transaction based on the merchant information. During the payment transaction, an amount of money corresponding to a price of the product may be transferred from a user payment account to a merchant payment account. The price of the product may be included into the product information. The payment transaction may be performed by sending payment data by a NFC unit of the WPD device to a merchant using a NFC.

In an example embodiment, the NFC may be used for payments for purchases made online and offline. A user of the WPD device 200 equipped with the NFC unit may perform transactions without authentication, or some authentication may be needed, such as a Personal Identification Number (PIN), before transaction is completed. The payment can be deducted from a pre-paid account of the user or charged directly to a bank account of the user. In example embodiment, the NFC unit may enable the WPD device 200 to establish radio communication with external devices by touching the WPD device 200 and the external device together or bringing them into proximity.

In an example embodiment, the camera 212 may be further operable to track a face, fingers, gestures, and other biometric personal data of the user. In turn, the processor may be operable to analyze the face, the fingers, the gestures, and the other biometric personal data tracked by the camera. Additionally, the processor may recognize speech and subtract a background noise from the speech.

The camera 212 may be further operable to perform an optical character recognition of a data. The data may include one or more of the following: a typewritten text, a printed text, an image, and the like. The data may be scanned from a document, such as a passport, an invoice, a bank statement, a computerized receipt, a business card, a mail, a printout of static-data, a book, a print publication, and so forth.

Figure 3:
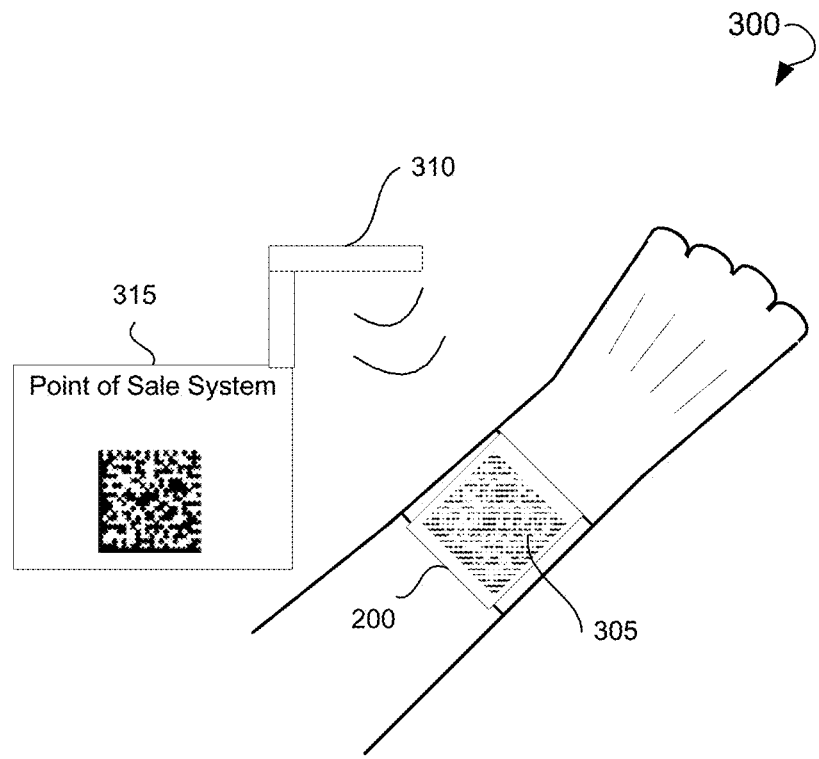
FIG. 3 illustrates an example of a wearable personal digital device for facilitating mobile device payments, personal use, and health care scannable by a Point-of-Sale system, in accordance with some embodiments.

In a further example embodiment, the WPD device 200 may be adapted to display a unique code to be scanned by a Point-of-Sale (POS) system. FIG. 3 shows a schematic representation 300 of scanning a barcode 305 displayed on the WPD device 200 by a barcode scanner 310 of the POS system 315. The barcode 305 may encode user payment information, such as a bank account, a payment card number, and so forth. The barcode 305 may be generated by a payment system (not shown) associated with the WPD device 200 or the external device. Therefore, the user may use the barcode 305 instead of a debit card or a credit card.

Referring back to FIG. 2, the front view 210 of the WPD device 200 shows an example embodiment, according to which the WPD device 200 includes a swipe card reader 214 communicatively coupled to the processor. The swipe card reader 214 may be located on either side of the WPD device 200, vertically or horizontally. The swipe card reader 214 may be operable to read data of a payment card. Upon reading, the data may be transmitted to the processor of the WPD device 200 or to the external device. The swipe card reader 214 may be used, for example, during performing payments on-line. Furthermore, the swipe card reader 214 may be used for providing user payment information, which may be further encoded into a barcode 216. The barcode 216 may be displayed on the display 204, e.g., in a store, for performing the payment transaction.

The biometric parameters sensed by the biometric sensors may be stored to the memory unit of the WPD device 200. According to another embodiment, the biometric parameters sensed by the biometric sensors may be transmitted to the external device for further processing or displaying on the external device. The processor may be operable to provide data associated with biometric parameters to be displayed on the display 204. The biometric parameters may include one or more of the following: a blood pressure, a heart rate, a glucose level, a body temperature, an environment temperature, arterial properties of the user, and the like. The biometric sensors may be disposed within the band. Based on detection that the one or more of the biometric parameters of the user exceed predetermined limits, the biometric sensors may be configured to produce the alarm. In an example embodiment, the biometric sensors include lenses operable to use infrared light-emitting diodes (LED) and visible-light LEDs to sense a heart rate of the user. In a further example embodiment, the biometric sensors may be operable to non-invasively monitor a glucose level. The glucose level may be monitored using a saliva testing. Wearable device may be integrated with one or more thin film silicon photonic biosensor that uses beams of light to detect tiny changes in the composition of a saliva or urine sample on the screen of wearable device or mobile device, which essentially looks at the level of binding between a DNA probe and target microRNA to figure out the level of microRNA in the sample. This can then provide clues to the presence of some types of cancer, cardiac disease, and other serious health issues via artificial intelligence (AI) big data analysis.

The biometric sensors may further include a skin contact sensor data engine. The skin contact sensor data engine may be operable to monitor a user electrocardiogram or the heart rate. The user electrocardiogram and the heart rate may serve as identification and personal data of the user. The skin contact sensor data engine may be further operable to prompt the user to enter a PIN after placing the WPD device 200 on the wrist. The skin contact sensor data engine may associate the PIN with the user electrocardiogram and the heart rate. Therefore, in case of placing the WPD device 200 on a wrist of another user, another user may be not authorized to user the WPD device 200 because a user electrocardiogram and a heart rate of another user may differ from those of the user of the WPD device 200.

A thermal infrared (IR) measurement of sensor may be used to investigate the potential of cancer detection. An adhesive sensor system worn on the skin that may automatically detect human falls and fatal diseases, the sensor, which may consist of a tri-axial accelerometer, a microcontroller and a Bluetooth Low Energy transceiver, can be worn anywhere on a human body to detect a specific biological analyte by essentially converting a biological entity into an electrical signal that can be detected and analyzed by using of biosensor in cancer and other fatal diseases detection and monitoring.

The haptic touch control actuator may be operable to produce a haptic feedback in response to one or more events. The one or more events may include receiving of the alert, receiving of a notification, a confirmation, movement of the WPD device 200, receiving of the user input, sensing of the one or more biometric parameters, and so forth. The haptic feedback may be sensed by the user body, such as a wrist of the user. The haptic feedback may have a plurality of feedback types. More specifically, each of the one or more events may be associated with one of the plurality of feedback types.

In a further example embodiment, the display 204 may be further operable to display data associated with the activity of the user. The activity of the user may include calories burned, sleep quality, breaths per minute, snoring breaks, steps walked, distance walked and the like. The activity of the user may be tracked by the activity tracking sensors of the WPD device 200. The activity tracking sensors may be operable to monitor user movements in a three-dimensional trajectory, identify type of user activity, identify a specific motion fingerprint of an exercise, evaluate user physical form, count repetitions, calculate calories burned, and so forth. In certain example embodiments, the activity tracking sensors may sense and track position of the user to identify the snoring of the user and provide a notification to the user, e.g. using the vibration, to force the user to change the position. In an example embodiment, the activity tracking sensors are operable to track snoring of the user and, based on tracking of the snoring, produce an alarm to the user to break snoring.

In an example embodiment, the WPD device 200 may further include a microphone (not shown). The microphone may be operable to sense voice data. The voice data may be obtained from the user. For example, the user may provide a user request using user voice. The voice data may include a voice command, a voice memo, a voice message, and the like. The voice data may be transmitted to the processor for further processing. In particular, the processor may be operable to recognize the voice data in order to obtain the user request. The user request may be transmitted to the external device.

In an example embodiment, the input unit 206 may include a clock crown located on any of lateral sides of the housing, an upper side of the housing, or a bottom side of the housing. The processor may be operable to sense the rotational motion of the input unit 206. For example, the user may rotate the input unit 206. Based on the sensing, the data displayed on the display 204 may be scrolled. Each action performed by the user on the input unit 206, such as direction of rotation (e.g., clockwise or counter clockwise), speed of rotation, pressing the input unit 206 towards the housing 202, or extending the input unit 206 outwards the housing 202, may correspond to a specific command.

In a further example embodiment, the processor of the WPD device 200 may be operable to control an operation of a camera of the external device. Furthermore, the processor may access audio files stored on the external device and wirelessly connect with earphones. Upon accessing the external device and connecting with the earphones, the processor may reproduce the audio files using the earphones. Therefore, the user of the WPD device 200 may listen to the music stored on the external device and control reproducing of the audio files using the WPD device 200.

In an example embodiment, the processor may be further operable to generate a code encoding user payment data and user personal data. The generation may be performed based on the user payment data and the user personal data stored in the memory unit of the WPD device 200. The processor may be further operable to prompt the user to touch the display to scan user fingerprints. Additionally, the processor may be further operable to determine a heart rate of the user using the biometric sensors. The processor may be further operable to compare the user fingerprints and the heart rate of the user with reference fingerprints and a reference heart rate. The reference fingerprints and the reference heart rate may be stored in the memory unit. The processor may detect a match of the user fingerprints with the reference fingerprints and of the heart rate of the user with the reference heart rate. Base of the detecting, the processor may provide the code to a merchant digital device for performing a payment transaction. Upon the payment transaction, a payment confirmation may be provided to the user. The payment confirmation may be provided using the haptic feedback.

In an example embodiment, the processor may be further operable to detect current user location, e.g. using a GPS unit. The processor may be operable to detect presence of premises associated with the user in proximity to the current user location. The premises may include a home, an office, a garage, a car, and the like. Based on the detecting, the processor may be operable to initiate unlocking of the premises.

In a further example embodiment, the processor of the WPD device 200 may be operable to detect presence of another WPD device in proximity to the WPD device 200. Based on the detecting, the processor may be operable to initiate data transmission between the WPD device 200 and another WPD device.

In an example embodiment, the processor may be further operable to receive, from the user, a content access request for at least one content item of content data stored in the memory unit of the WPD device 200. The processor may read access rules stored in the memory unit. The access rules may be associated with use of the at least one content item. Based on the access rules, the processor may be operable to determine that an access to the at least one content item is permitted. Based on the determining, the at least one content item may be reproduced to the user.

The content data may include audio data, video data, text, software, and game data. The WPD device 200 may act as a data carrier and include an interface for sending and receiving data. The memory unit may be operable to store received content data, provide payment validation data to the external device, store a record of access made to the stored content data, and the access rules for controlling access to the stored content data. The processor may be further operable to access control data and supplementary data including hot links to websites and advertising data. Payment data, the stored content data and access rules data may be used to reduce a risk of an unauthorized access to the content data.

The WPD device 200 may further include a battery (not shown) disposed in the housing. Additionally, the WPD device 200 may include a magnetic inductive charging unit (not shown). The magnetic inductive charging unit may be operable to magnetically connect to the housing and wirelessly connect to the battery. The magnetic inductive charging unit may be operable to wirelessly transfer energy to the battery. In some example embodiments, the magnetic inductive charging unit may be integrated into the housing. Once connected magnetically to the back of the WPD device 200, the connection of magnetic inductive charging unit may be seamless and need no additional alignment by the user.

The WPD device 200 may further include a light indicator operable to show a light indication in response to receiving data from an external device. Upon a predetermined movement of the user body, such as raising a hand, the light indication may stop showing the light indication and initiate the display to display the data received from an external device.

In example embodiments, the housing may have round, square, rectangular and other shape. Therefore, when the WPD device 200 is paired with the external device, a plurality of applications running on the external device may be visualized on the display of the WPD device 200 using a form factor specific to the form and size of the housing.

Figure 4:
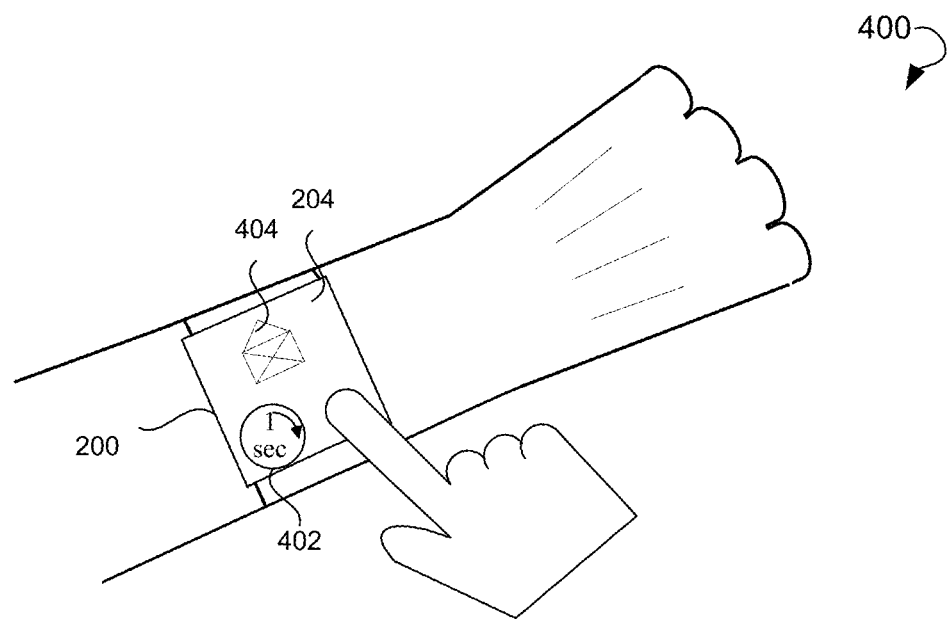
FIG. 4 shows user interaction with a display of a wearable personal digital device for facilitating mobile device payments, personal use, and health care, in accordance with some embodiments
Figure 4:
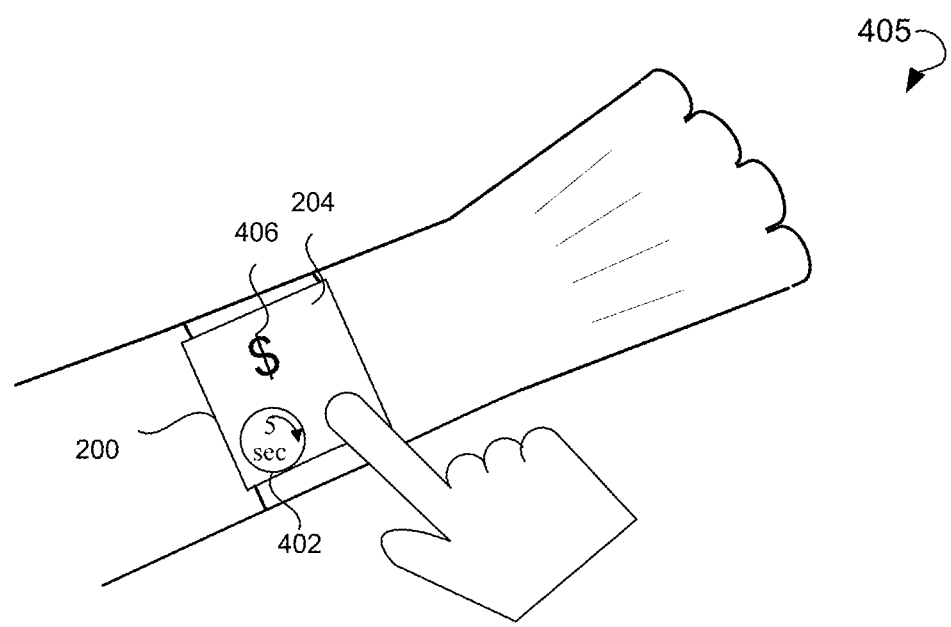

FIG. 4 shows diagrams 400 and 405 that represent user interaction with the display 204 of the WPD device 200. The user may provide the user input by pressing the display 204 for a predetermined time. The processor may estimate time of the user input. The time of user input may correspond to a specific command. The memory unit may store a table representing relationship between duration of pressing and a plurality of commands. For example, as shown on the diagram 400, the user may press the display 204 for 1 second. The time of 1 second may correspond to a message mode. Therefore, based on the time of 1 second, the processor may select a command from the table, such as initiation of the message mode. The processor may further perform the selected command, namely, initiate the message mode. During the time when the user presses the display 204, a timer 402 may be displayed on the display 204. The timer 402 may show the time the user presses the display 204. Additionally, an icon 404 may be displayed. The icon 404 may represent a command corresponding to the time currently shown on the timer 402. For example, the icon 404 may represent the message mode.

In another example embodiment, as shown on the diagram 405, the user may press the display 204 for 5 seconds. The time of 5 seconds may correspond to a payment mode. Therefore, based on the time of 5 second, the processor may select a command from the table, such as initiation of the payment mode. The timer 402 may show the time the user presses the display 204, namely 5 seconds. Additionally, an icon 406 representing the payment mode may be displayed.

Referring back to FIG. 2, the WPD device 200 may further include a vibration unit (not shown) in communication with the processor. The vibration unit may be activated in response to receiving the data from the external device to notify the user about receipt of the data. For example, upon receipt of the message by the remote device, the vibration unit of the WPD device 200 may be activated.

In an example embodiment, the band 208 of the WPD device 200 may be detachable. The detached view 220 shows the band 208 detached from the housing 202 of the WPD device 200.

The WPD device 200 may further include a GPS unit (not shown) configured to track geographical location of the device. Such information may be applied for spatial and positional awareness tracking, monitoring position of a child, a senior, or a patient. In some embodiments, the WPD device 200 may connect to one or more external devices (for example, other WPD devices), synchronize with the one or more external devices in real time, tracks a geographical location of the one or more external devices in real time, and provide communication capabilities using an embedded emergency button configured to give a medical alert signal, a request for help signal, or another informational signal. Thus, users may track geographical location of each other.

In some embodiments, access to the WPD device 200 may be protected by a password, a Personal Identification Number code, biometric authorization, and so forth. Biometric authorization may be performed using one or more biometric sensors and may include fingerprint scanning, palm scanning, face scanning, retina scanning, heart rate sensing, and so forth. In some embodiments, fingerprint scanning may be performed using a fingerprint reader integrated in the WPD device 200 or detachably connected to the WPD device. The scanned fingerprint may be matched to one or more approved fingerprints stored in the memory unit of the WPD device 200. The access to the device may be granted if the scanned fingerprint matches one of the stored fingerprints, otherwise access may be denied.

The payment transaction may be associated with a NFC and be performed for purchases online and offline. A payment associated with the payment transaction may be transferred from a pre-paid account of the user or charged to a mobile account of the user or a bank account of the user. The payment may include at least a one-touch and one-scan payment for street parking in demarcated areas. The payment may be performed using a license plate, transponder tags, barcode stickers, and reading the code from the display. A merchant may use a combination of the NFC and the code on the display for performing the one-touch and one-scan payment. The NFC may be used to establish radio communication with the external device by touching the housing of the WPD device 200 and the external device or bringing the housing of the WPD device 200 and the external device into proximity, such a distance of up to 10 centimeters. The processor may be operable to operate in three modes, such as an NFC target mode when the WPD device 200 is acting as a credential, a NFC initiator mode when the WPD device 200 is acting as a reader, and an NFC peer-to-peer mode. The payment may be further associated with advertisement tags, two-dimensional barcodes, and ultra-high frequency tags. The processor may be operable to be connected to a cloud. User credentials may be provisioned over the air. The payment may be associated with a payment application associated with the processor to control transferring of the payment and access payment readers. The NFC unit may be operable to connect to a third-party NFC device with a server for data.

The processor may be associated with an operating system operable to pair with third-party applications running on the external device. The processor may integrate a third-party developer technology and the third-party applications and notifications into a form factor. The processor may be operable to download applications. The WPD device 200 may act as or be associated with smart textiles, an activity tracker, a smartwatch, smartglasses, a GPS watch, mixed reality, computer-mediated reality, clothing technology, Smart closing, healthcare, augmenter reality, and smart and connected devices.

The WPD device 200 may be adapted to enable a Bluetooth low energy payment. The WPD device 200 may be further associated with one or more of a transactional payment based on Unstructured Supplementary Service Data, Short Message Service, direct operator billing, a credit card mobile payment, an online wallet, a QR code payment, contactless NFC, a cloud-based mobile payment, an audio signal-based payment, a Bluetooth Low Energy signal beacon payment, an in-application payment, a Software Development Kit payment, an Application Programming Interface payment, a social networking payment, and a direct carrier and bank co-operation.

Figure 5:
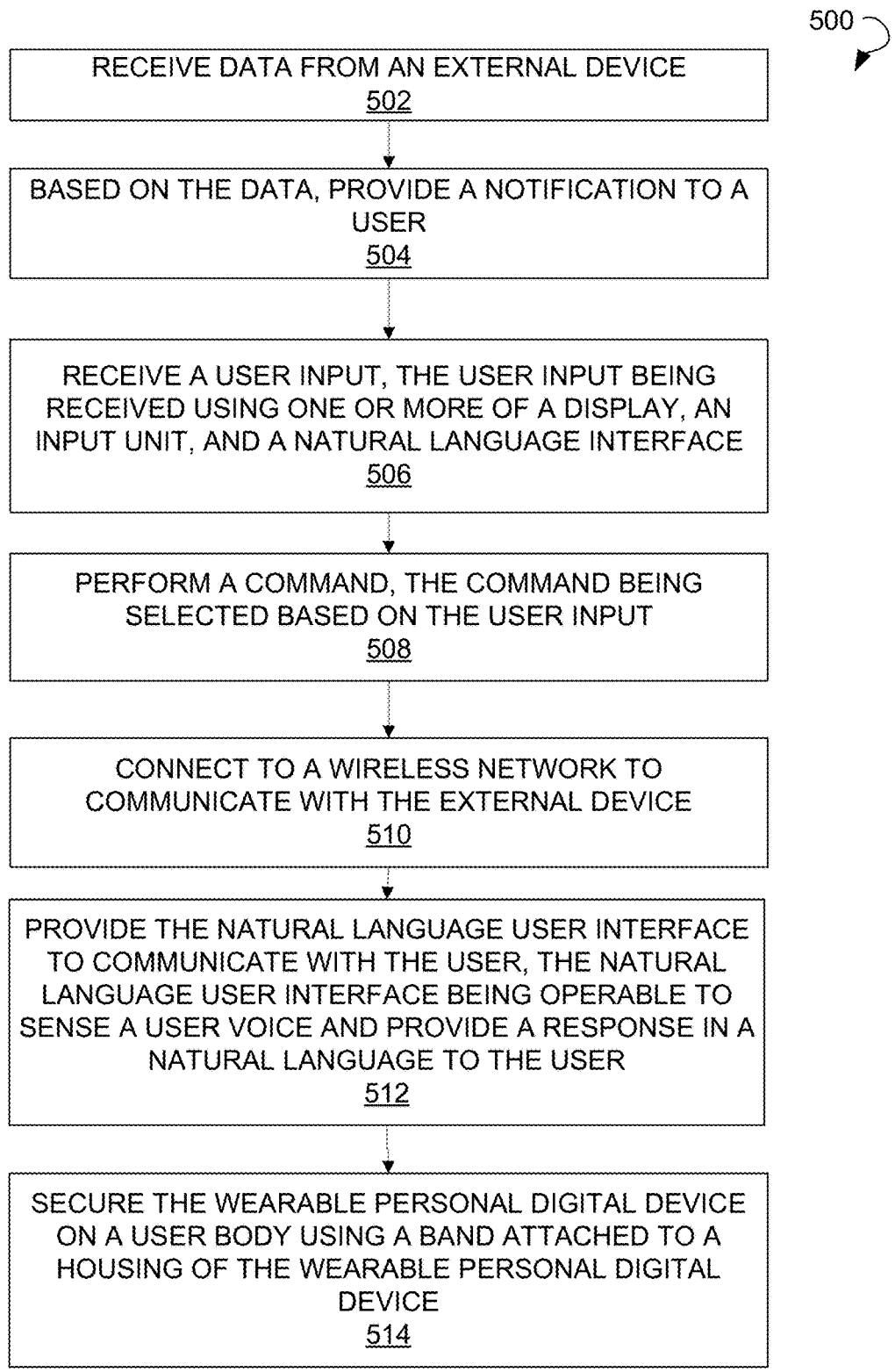
FIG. 5 is a flow chart illustrating a method for facilitating user interaction with a wearable personal digital device for facilitating mobile device payments, personal use, and health care, in accordance with certain embodiments.

FIG. 5 is a flow chart illustrating a method 500 for facilitating user interaction with a WPD device, in accordance with certain embodiments. The method 500 may start with receiving data from an external device at operation 502. Based on the data, a notification may be provided to a user at operation 504. In an example embodiment, providing of the notification includes one or more of the following: providing a vibration, providing a sound, and providing a light indication. At operation 506, a user input may be received. In an example embodiment, the user input may be received using a display, an input unit of the WPD device, or a natural language user interface. At operation 508, a command may be performed. In an example embodiment, the command selected based on the user input may be performed. At operation 510, the WPD device may be connected, using a communication circuit communicatively coupled to the processor of the WPD device, to a wireless network to communicate with the external device.

At operation 512, the natural language user interface may be provided to communicate with the user. The natural language user interface may be operable to sense a user voice and provide a response in a natural language to the user. The WPD device may be secured on a user body at operation 514 using a band attached to a housing of the WPD device.

In an example embodiment, the method 500 may further include capturing, by a camera communicatively coupled to the processor, a code. The code may include a linear dimensional code, a two-dimensional code, a snap tag code, or a QR code. The method 500 may further include reading the code to obtain product information and merchant information encoded in the code. Based on the merchant information, a payment transaction may be initiated.

Additionally, the method 500 may include activating the display based on one or more of the following: a movement of a user hand, a movement of the user body, a gesture performed by the user in proximity to the display, user voice, and the like. In an example embodiment, the method 500 further includes storing the biometric parameters sensed by the one or more biometric sensors to the memory unit of the WPD device. Alternatively, the biometric parameters sensed by the one or more biometric sensors may be transmitted to the external device.

Additionally, the method 500 may include sensing, by a microphone, voice data. The voice data may be obtained from the user and may include a voice command, a voice memo, or a voice message. The voice data may be transmitted to the processor of the WPD device for further processing. Additionally, the voice data may be recognized to obtain a user request. The user request may be transmitted to the external device.

In an example embodiment, the method 500 may further include estimating time of the user input. The user input may include pressing the display by the user. Based on the time, a command may be selected from a table representing relationship between the time of pressing and a plurality of commands. The selected command may be further performed by the processor.

Additionally, the method 500 may include displaying, by the display, data associated with the activity of the user. The activity of the user may include calories burned, sleep quality, breaths per minute, snoring breaks, steps walked, and distance walked. Tumor DNA to be used as a marker for screening, early detection, and monitoring, traces of RNA from cancer cells can be found in a drop of saliva, the RNA is a molecule that plays a key role in the transcription of DNA, the mobile and wearable device screen process by which the genetic material is read in order to detect the proteins by detecting genetic mutations in a protein from epidermal factor receptor, by examining RNA in samples on mobile and wearable screens, wherein it is therefore possible to tell what sorts of processes are going on inside a cell by seeking out fragments of tumor RNA in saliva, including those associated with cancer. Furthermore, wearable device may be integrated with one or more thin film silicon photonic biosensor that uses beams of light to detect tiny changes in the composition of a saliva or urine sample on the screen of wearable device or mobile device, wherein which essentially looks at the level of binding between a DNA probe and target microRNA to figure out the level of microRNA in the sample, wherein this may provide clues to the presence of some types of cancer, cardiac disease, and other serious health issues via artificial intelligence (AI) big data analysis. Biosensors designed to detect a specific biological analyte by essentially converting a biological entity (ie, protein, DNA, RNA) into an electrical signal that can be detected and analyzed by using of biosensors in cancer detection and monitoring. The biosensors can be designed to detect emerging cancer biomarkers and to determine drug effectiveness at various target sites. The biosensor may have the potential to provide fast and accurate detection, reliable imaging of cancer cells, and monitoring of angiogenesis and cancer metastasis, and the ability to determine the effectiveness of anticancer chemotherapy agents. The method 500 may further include providing data associated with the one or more biometric parameters to be displayed on the display. The one or more biometric parameters may include one or more of the following: a blood pressure, a heart rate, a glucose level, a body temperature, an environment temperature, and arterial properties.

The wearer may monitor CAR-T cell therapy by separating the peripheral blood of the bearer patient immune T cells in vitro sterile culture, and then genetically engineered and modified, it is based on the type of tumor specificity of patients suffering from genetic modification and in vitro expansion, and finally the wearer patient reinfusion body, achieve the purpose of killing tumor cells. The wearer may further monitor CAR-T cell preparation, insert CAR molecular DNA be integrated into human chromosome 19 on the first intron AAVSl site, the donor DNA sequence provided in the CAR molecule containing a sequence upstream of the receptor sequences and AAVS1 cut left arm sequence homology, CAR downstream molecule containing poly-A sequence and AAVS1 the right arm sequence homology. The wearer furthermore monitor gene edited T cells applications to use the antibody molecules of various types of tumor surface antigens into the application of human T cell genome AAVS1 sites. To avoid potential off-target effects, a mutant enzyme of Ni ckase Cas9 may be used to only cut off a strand of DNA, the single-stranded gap will promote homologous recombination, therefore, to insert CAR molecules precisely integrated into human T cell genome specific "safe harbor" sites, which may not affect the function of any normal human gene, avoiding the use of viral vectors security risks and exogenous gene transit may insert a series of fatal risk of genetic toxicity and immunogenicity of the genome, wherein may integrate various types of tumor surface antigen receptor to human T cell genome AAVS1 site express specific receptors for all types of tumor-specific T cells recognize and kill tumor cells. The wearer may monitor a chimeric antigen receptor (CAR) T cells and a preparation method can allograft, aimed at resolving existing T cell separation difficulties from patient own self, who cannot effectively kill tumor cells and mixed with the issue of tumor cells. Another kind T cells can allograft chimeric T cell antigen receptor, said chimeric T cell antigen receptors including T cell receptors and a chimeric antigen, wherein the T cell is a genetically engineered allogeneic transplantation can T cells. The allograft may be chimeric T cell antigen receptor, wherein the T cells through gene knockout in a specific point of genetically modified T cells. The allograft may be chimeric T cell antigen receptor, wherein said specific gene of TCR gene, including the TCR [alpha] chain and a β chain, said genetically modified specifically: α in the TCR and corresponding foreign gene encoding β-chain of one or two chain constant region exon by gene knockout point, the TCR of T cells is not active, and thus T cells can be allogeneic. The allograft may be chimeric T cell antigen receptor, wherein said chimeric antigen receptor by a scFv antigen binding sequence, a transmembrane sequence, and intracellular signal transduction sequence. The allograft may be chimeric T cell antigen receptor, wherein said scFv antigen binding sequence comprises a light chain variable region sequence and a heavy chain variable region sequence. The allograft may be chimeric T cell antigen receptor, wherein the transmembrane sequence is CD8, wherein said intracellular signal transduction sequence comprising the CD28 extracellular domain sequence, the sequence and the intracellular domain of 4-1BB intracellular CD3G domain sequences. A species, may allograft chimeric antigen receptor T cells, which comprises of the TCR α and β chains of one or both chains constant outside the corresponding region of the gene coding exon, the T cells TCR is not active, and then be able to obtain allogeneic T cells, wherein furthermore carrying the chimeric receptor antigen lentivirus infection can be obtained by the above-described allogeneic T cells can be obtained after completion of infection allogeneic chimeric T cell antigen receptor. The wearer may monitor T cells genetically engineered, in turn, can make this T cell allografts without causing immune rejection. Then this will not produce allograft immune rejection T cell binding third-generation CAR can prepare a allograft universal chimeric antigen receptor T cells to tumor therapy.

In an example embodiment, the method 500 may further include sensing a rotational motion of the input unit. The input unit may be rotated by the user. Based on the sensing, the data displayed on the display may be scrolled. Additionally, the method 500 may include activating a vibration unit in response to receiving the data from the external device to notify the user about receipt of the data.

Figure 6:
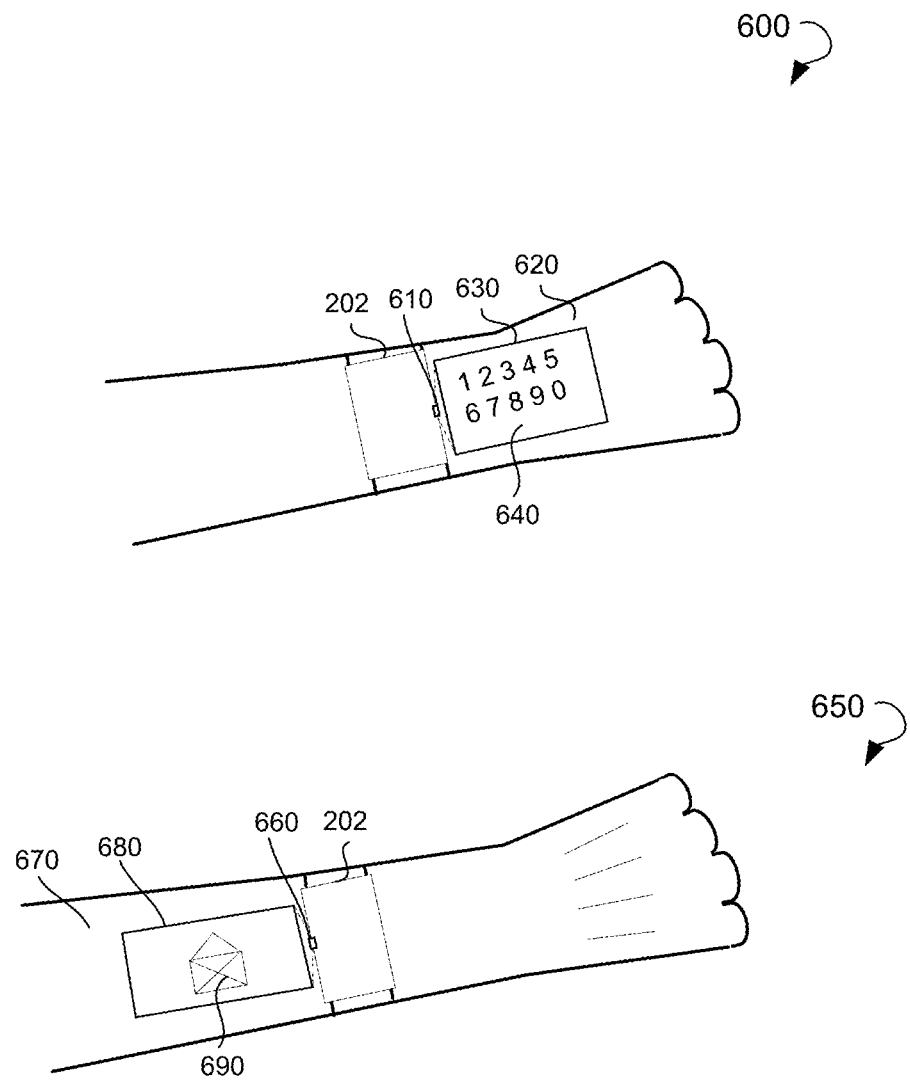
FIG. 6 illustrates an example of wearable personal digital devices for facilitating mobile device payments, personal use, and health care, in accordance with some embodiments.

FIG. 6 shows schematic representations of WPD devices 600 and 650, according to example embodiments. The WPD device 600 may include a housing 202 that may enclose the elements of the WPD device 600 as described above with reference to FIG. 2. The WPD device 600 may include a projector 610. The projector 610 may project a data onto a viewing surface 620 to form a display area 630. The display area 630 may serve as a further display of the WPD device 600. The viewing surface 620 may include a hand of the user. The data shown on the display area 630 may include any data requested by the user or any incoming notifications or alerts, including a virtual keyboard, a notification of the external device, time, data requested by the user, a caller name, a text message, a reminder, a social media alert, an email, a weather alert, and the like. FIG. 6 shows a virtual keyboard 640 displayed on the hand of the user.

The WPD device 650 may include a housing 202 that may enclose the elements of the WPD device 600 as described above with reference to FIG. 2. The WPD device 650 may include a projector 660. The projector 660 may project a data onto a viewing surface 670 to form a display area 680. The display area 680 may serve as a further display of the WPD device 650. The data shown on the display area 680 may include a message 690.

As shown on FIG. 6, the projector may be disposed on any side of the housing 202. More specifically, the display area 630 may be provided to the right from the wrist of the user (as in the WPD device 600) or the display area 680 may be provided to the left from the wrist of the user (as in the WPD device 650).

Figure 7:
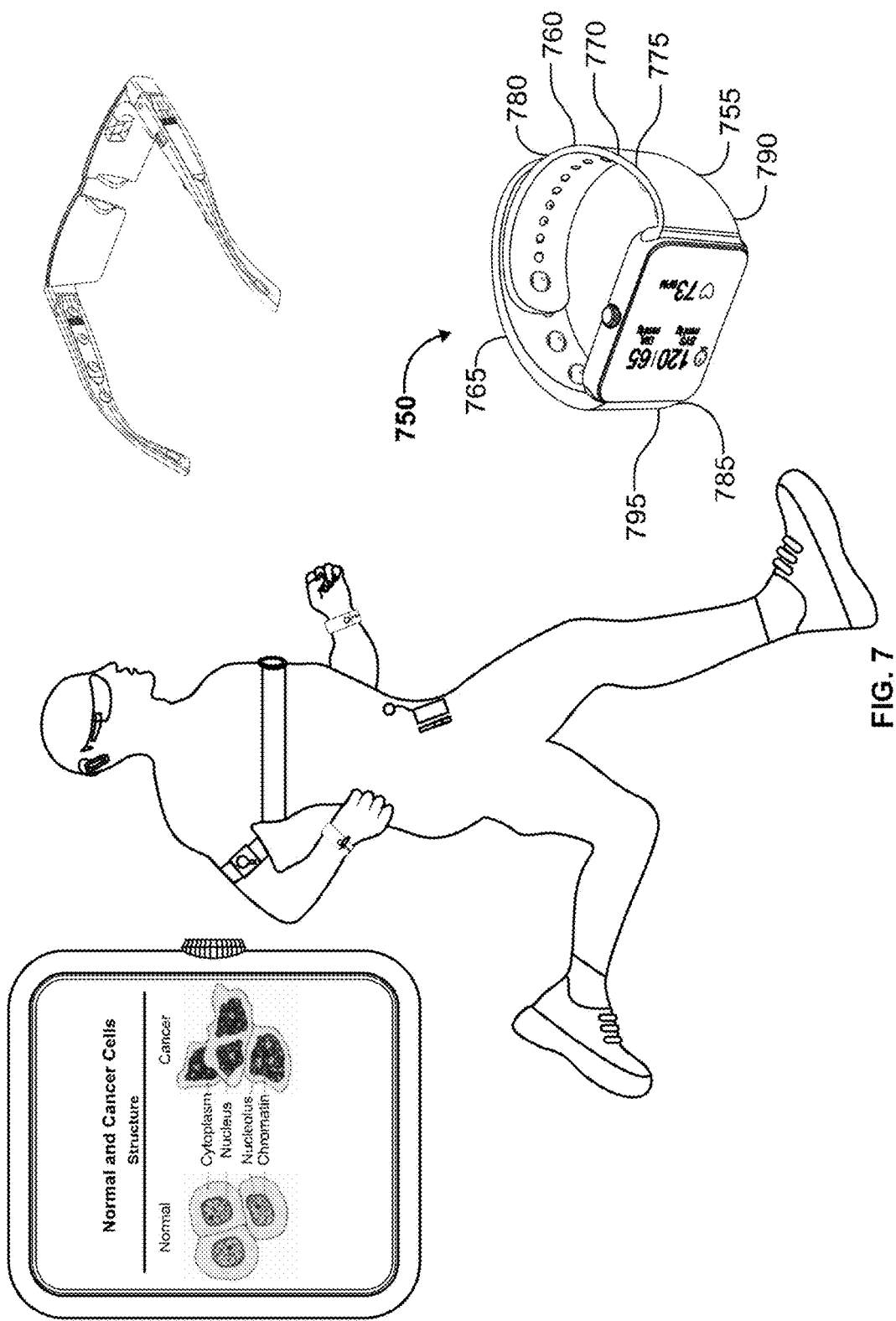
FIG. 7 illustrates an example of wearable personal digital devices for facilitating mobile device payments, personal use, and health care, in accordance with some embodiments.

FIG. 7 shows a man running and wearing various wearables with a sensor, e.g. smart glasses, smartwatch, etc. The sensor consists of a tri-axial accelerometer, a microcontroller and a Bluetooth Low Energy transceiver. Cancer may be detected using Temperature Variation and Radiation Analysis (TVRA) via wearable device, which has grown tangibly due to many factors, such as at least life expectancies increase, personal habits and ultraviolet radiation exposures. The smartwatch can display various medical parameters received from the wearables and also display differences between normal and cancerous cell structure.

FIG. 7 further shows the WPD device 750, which may be configured to be rolled around a wrist of the user. The WPD device 750 may include a processor 755, a projector 760, activity tracking sensors 765, a communication circuit including a Bluetooth module 770 or a Wi-Fi module 775, a haptic touch control actuator 780, a memory unit 785, an indicator 790, such as a LED, and a charging unit 795.

Figure 8:
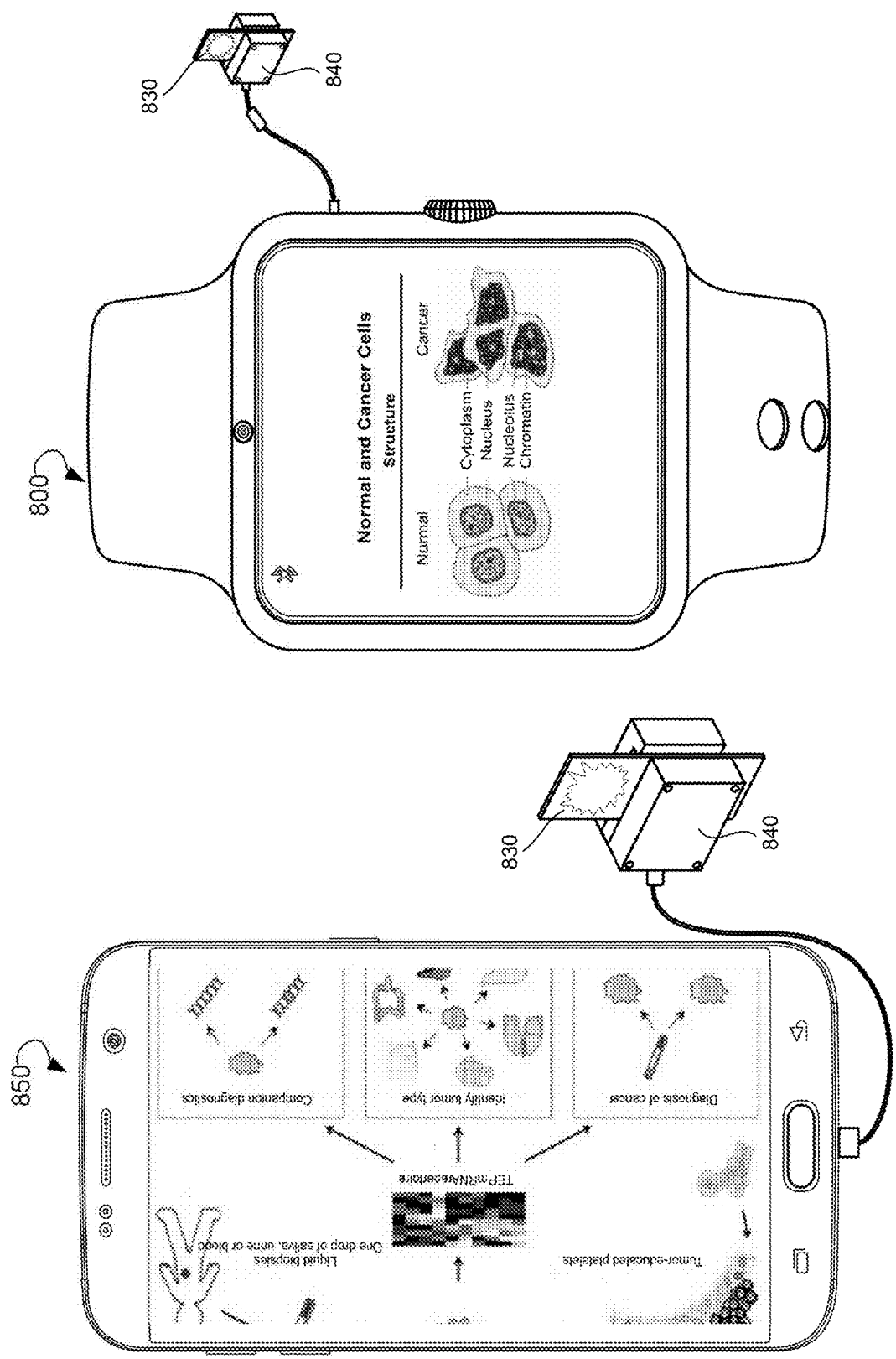
FIG. 8 illustrates an example of wearable personal digital devices for facilitating mobile device payments, personal use, and health care, in accordance with some embodiments.

FIG. 8 shows a mobile device 850 and smartwatch 800, which are wire connected to a thin film silicon photonic biosensor 840. The biosensor 840 may use beams of light to detect tiny changes in the composition of a saliva or urine sample on a thin film 830. The film 830 when pressed against the skin may create changes in electrical current and light (ECL) that can be captured by a high-quality digital camera of a wearable device. Normal and cancerous cell structures are displayed on a screen of the mobile device 850 and smartwatch 800.

Figure 9:
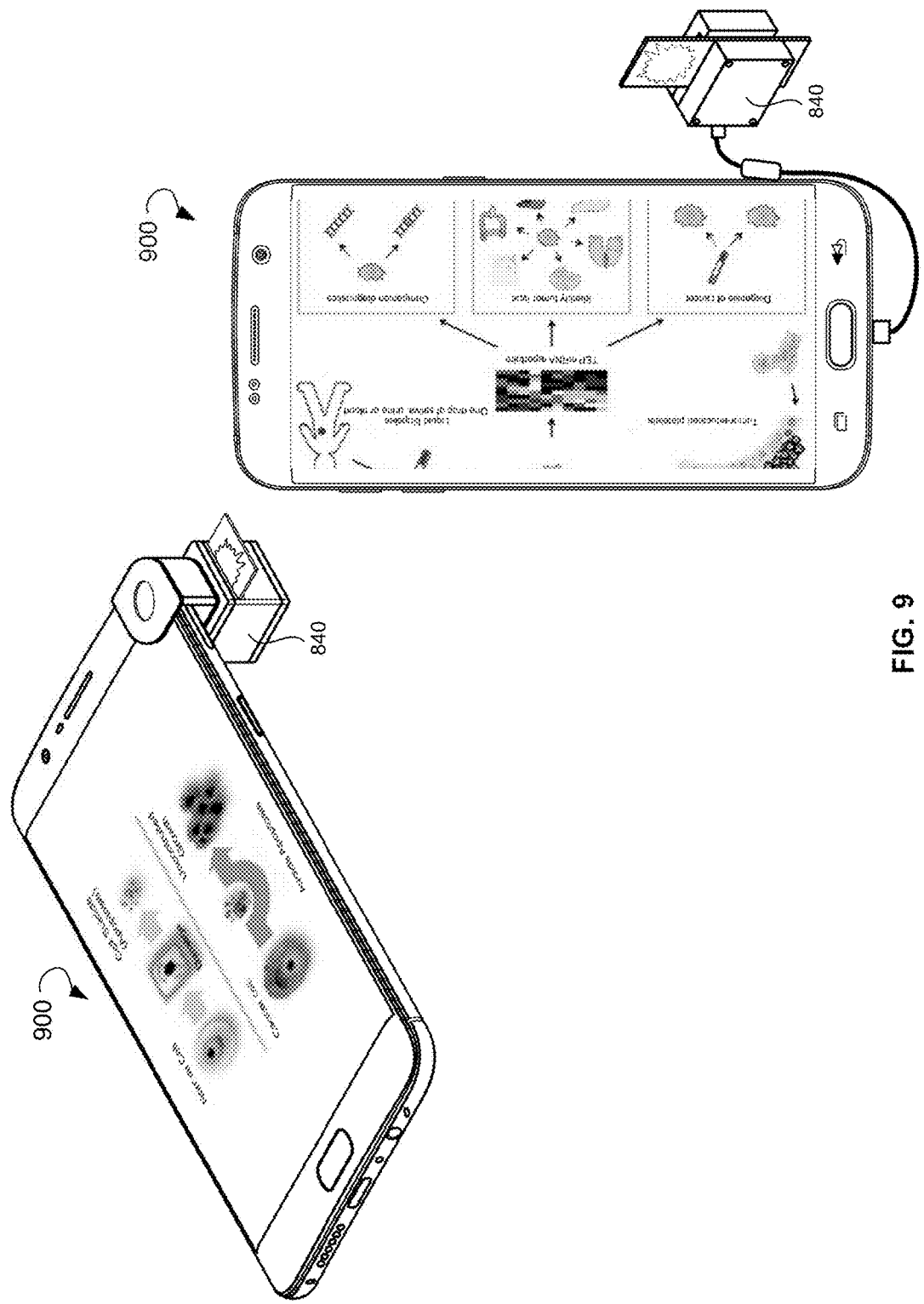
FIG. 9 illustrates an example of wearable personal digital devices for facilitating mobile device payments, personal use, and health care, in accordance with some embodiments.

FIG. 9 shows a mobile device 900 which may be connected to a thin film silicon photonic biosensor 940 by wire or wirelessly.

Thus, various WPD devices for facilitating mobile device payments and personal use and methods for facilitating user interaction with the WPD devices have been described. Although embodiments have been described with reference to specific example embodiments, it will be evident that various modifications and changes may be made to these embodiments without departing from the broader spirit and scope of the system and method described herein. Accordingly, the specification and drawings are to be regarded in an illustrative rather than a restrictive sense.

What is claimed is:

1. A wearable personal digital device for facilitating mobile device payments, personal use, and health care, the device comprising:
  a processor being operable to:
    receive data from an external device;
    based on the data, provide a notification to a user;
    receive a user input;
    perform a command, the command being selected based on the user input;
    provide a natural language user interface to communicate with the user, the natural language user interface being operable to sense a user voice and provide a response in a natural language to the user;
  a near field communication (NFC) unit communicatively coupled to the processor;
  a display communicatively coupled to the processor, the display including a touchscreen, wherein the display includes a force sensor, wherein the force sensor is operable to sense a touch force applied by the user to the display and calculate coordinates of a touch by the user, and further operable to analyze the touch force and, and based on the touch force, select a tap command or a press command based on a predetermined criteria, wherein each of the tap command and the press command is executed based on a duration of the touch of the user using one or more applications running on the wearable personal digital device;
  a projector communicatively coupled to the processor, the projector being operable to project a data onto an arm of the user, the data including a virtual keyboard operable to provide inputs to the processor and one or more of the following: the notification, a time data, data requested by the user, a caller name, a text message, a reminder, a social media alert, an email, and a weather alert;
  a timepiece unit communicatively coupled to the processor and configured to provide the time data;
  one or more activity tracking sensors communicatively coupled to the processor to track activity of the user, wherein the one or more activity tracking sensors are operable to track snoring and, based on tracking of the snoring, produce an alarm to break snoring;
  a memory unit communicatively coupled to the processor;
  a communication circuit communicatively coupled to the processor and operable to connect to a wireless network and communicate with the external device;
  a housing adapted to enclose at least the processor, the display, the one or more activity tracking sensors, the memory unit, and the communication circuit;
  an input unit communicatively coupled to the processor, wherein the input unit extends from the housing and is configured to perform one or more of a rotational motion and a linear motion, wherein the user provides commands to the processor by moving the input unit; and
  a band adapted to attach to the housing and to secure the wearable personal digital device for facilitating mobile device payments, personal use, and health care on a user body, wherein the wearable personal digital device comprises a wristwatch;
  biometric sensors disposed within the band and operable to sense one or more biometric parameters of the user, wherein based on detection that the one or more of the biometric parameters exceed predetermined limits, the biometric sensors are configured to produce the alarm, wherein the biometric sensors include lenses operable to use infrared light-emitting diodes (LED) and visible-light LEDs to sense a heart rate of the user, wherein the biometric sensors include a skin contact sensor data engine, the skin contact sensor data engine being operable to monitor a user electrocardiogram and the heart rate of the user, the user electrocardiogram and the heart rate being identification and personal data of the user, wherein the skin contact sensor data engine is operable to prompt the user to enter a personal identification number and the processor is operable to associate the personal identification number with both the user electrocardiogram and the heart rate obtained after the wearable personal digital device has been secured to a wrist of the user, wherein processor stores the obtained electrocardiogram and heart rate in the memory unit as a reference electrocardiogram and reference heart rate; and
  an adhesive sensor system wearable on a skin of the user body, consisting of a tri-axial accelerometer, a microcontroller and a Bluetooth Low Energy transceiver, the adhesive sensor system being operable to detect falls of the user based on data provided by the tri-axial accelerometer;
  a thermal infrared (IR) sensor worn on the skin of the user body and operable to sense a radiation having a range of wavelengths from 800 nanometer to hundreds of micrometers emitted by the user body;
  a biosensor integrated with integrated with the wearable personal digital device, the biosensor including a thin-film silicon photonic biosensor, the biosensor including at least a film made of nanoparticles and polymers, wherein the biosensor uses beams of light to detect changes in a composition of a saliva sample and an urine sample of the user placed on the film, each of the saliva sample and the urine sample comprising a biological entity including one or more of a protein, a deoxyribonucleic acid (DNA), and a ribonucleic acid (RNA), wherein the detecting the changes includes determining a level of binding between a DNA probe and a target microRNA to figure out a level of the target microRNA in the saliva sample and the urine sample, wherein the level of the target microRNA is indicative of a presence of types of cancer, cardiac disease, and health issues, and wherein the level of target microRNA in the saliva sample and the urine sample is displayed on the touchscreen of the wearable personal digital device;
  wherein data associated with the level of binding determined using the biosensor and the range of the wavelengths detected using the IR sensor are transmitted to the external device for further analysis;
  a haptic touch control actuator operable to produce a haptic feedback in response to one or more events, the one or more events including receiving of the alert, receiving of a notification, a confirmation, movement of the wearable personal digital device for facilitating mobile device payments, personal use, and health care, receiving of the user input, and sensing of the one or more biometric parameters, the haptic feedback being sensed by the user body, wherein the haptic feedback includes a plurality of feedback types, each of the one or more events being associated with one of the plurality of feedback types, the plurality of feedback types including at least one-time vibration and two-times vibration;

a battery disposed in the housing of the wearable personal digital device;

a magnetic inductive charging unit being operable to magnetically connect to the housing and wirelessly connect to the battery, wherein the magnetic inductive charging unit is operable to wirelessly transfer energy to the battery, wherein the magnetic inductive charging unit is integrated into the housing;

wherein the user input is received using one or more of the display, the input unit, and the natural language user interface;

wherein the wearable personal digital device further comprises a camera communicatively coupled to the processor and operable to capture an optical code of a product for sale by a merchant, the optical code including one or more of the following: a linear dimensional barcode, a two-dimensional barcode, a snap tag code, and a Quick Response (QR) code;

wherein the processor is further operable to read the optical code to obtain a product information and a merchant information encoded in the optical code, and based on the merchant information, perform a payment transaction, wherein the processor is configured to perform the payment transaction by sending payment data by the NFC unit to a merchant NFC unit;

wherein the wearable personal digital device further comprises a swipe card reader communicatively coupled to the processor and operable to read data of a payment card swiped there through, the data being transmitted to the processor; and wherein the processor of the wearable personal digital device is further operable to:
 generate, based on the user payment data and the user personal data, a code encoding the user payment data and the user personal data, the user payment data and the user personal data being stored in the memory unit;
 prompt the user to touch the display to scan user fingerprints;
 determine the heart rate and the electrocardiogram of the user using the biometric sensors;
 compare the scanned user fingerprints, determined heart rate and determined electrocardiogram with reference fingerprints stored in the memory unit, the reference heart rate, and the reference electrocardiogram;
 detect a match of the scanned user fingerprints with the reference fingerprints, the determined heart rate with the reference heart rate, and the determined electrocardiogram with the reference electrocardiogram; and
 wherein the processor is further configured to provide, after the detecting of the matches, the code via the display of the device to a merchant digital device, wherein the merchant digital device reads the code for performing the payment transaction; and
wherein the processor, upon performing the payment transaction, provides a payment confirmation to the user, the payment confirmation being provided using the haptic feedback;

and wherein the display is further operable to display data associated with the activity of the user detected by the activity sensors, the detected activity of the user including calories burned, sleep quality, breaths per minute, snoring breaks, steps walked, and distance walked.

2. The device of claim 1, wherein the camera is further operable to:
 track a face, fingers, gestures, and other biometric personal data; and
 the processor is further operable to:
  analyze the face, the fingers, the gestures, and the other biometric personal data tracked by the camera;
  recognize speech; and
  subtract a background noise from the speech.

3. The device of claim 1, wherein the camera is further operable to perform an optical character recognition of a data, the data including one or more of the following: a typewritten text, a printed text, and an image, the data being scanned from a document, the document including one or more of the following: a passport, an invoice, a bank statement, a computerized receipt, a business card, a mail, a printout of static-data, a book, and a print publication.

4. The device of claim 1, wherein the display is operable to be activated based on one or more of the following: a movement of a user hand, a movement of the user body, a gesture performed by the user in proximity to the display, and a user voice.

5. The device of claim 1, wherein the communication circuit includes one or more of the following: a wireless transceiver, a Bluetooth module, a Wi-Fi module, and a communication port, wherein the communication port includes one or more of the following: a universal serial bus port, a parallel port, an infrared transceiver port, and a radiofrequency transceiver port.

6. The device of claim 1, further comprising:
 a microphone operable to:
  sense voice data, the voice data being obtained from the user and including a voice command, a voice memo, or a voice message; and
  transmit the voice data to the processor; and
 a light indicator being operable to show a light indication in response to receiving the data from the external device, wherein upon a predetermined movement of the user body the light indication stops showing the light indication and initiates the display to display the data received from an external device.

7. The device of claim 6, wherein the processor is further operable to:
 recognize the voice data to obtain a user request; and
 transmit the user request to the external device, wherein a plurality of applications running on the external device are visualized on the display using a form factor.

8. The device of claim 1, wherein the processor is further operable to:
 estimate time of the user input, the user input including pressing the display by the user;
 based on the time, select a command from a table, the table representing relationship between duration of pressing and a plurality of commands; and
 perform the command.

9. The device of claim 1, wherein the input unit includes a clock crown located on one or more of the following: a lateral side of the housing, an upper side of the housing, and a bottom side of the housing.

10. The device of claim 9, wherein the processor is further operable to:

sense the rotational motion of the input unit, the input unit being rotated by the user; and based on the sensing, scroll the data displayed on the display.

11. The device of claim 1, further comprising a vibration unit in communication with the processor, the vibration unit being activated in response to receiving the data from the external device to notify the user about receipt of the data.

12. The device of claim 1, wherein the notification is provided via one or more of the following: a vibration, a sound, and a light indication.

13. The device of claim 1, wherein the processor is further operable to:

detect absence of interaction of the user with the display, wherein the detection is made based on an eye tracking of the user, a head tracking of the user, and a spatial position of the housing; and based on the detecting, dim the display.

14. The device of claim 1, wherein the processor is further operable to:

activate the display based on a spatial position of the housing or a gesture of the user body.

15. The device of claim 1, wherein the processor is further operable to:

receive, using the natural language user interface, a map request from the user;

in response to the map request, display, using the display, a map and a route depicted on the map; and provide, using the haptic feedback, an indication associated with the route to the user.

16. The device of claim 1, wherein the processor is further operable to:

analyze a message received by the external device, the analyzing including one or more of the following: parsing a text; reading an image, and recognizing a voice;

based on the analyzing, display one or more possible replies;

receive, from the user, a selection of a reply from the one or more possible replies; and based on the selection, send the reply to the external device.

17. The device of claim 1, wherein the processor is further operable to:

analyze the activity of the user; and based on the analyzing, display one or more diagrams on the display, the one or mode diagrams representing one or more activity types of the user.

18. The device of claim 1, wherein the processor is further operable to:

control an operation of a camera of the external device;

access audio files stored on the external device;

wirelessly connect with earphones; and reproduce the audio files using the earphones.

19. The device of claim 1, wherein the payment transaction performed by the processor is associated with a NFC, the payment transaction being performed for purchases online and offline, wherein a payment associated with the payment transaction is transferred from a pre-paid account of the user or charged to a mobile account of the user or a bank account of the user;

wherein the payment includes at least a one-touch and one-scan payment for street parking in demarcated areas, the payment being performed using a license plate, transponder tags, barcode stickers, and reading the code from the display;

wherein a merchant uses a combination of the NFC and the code on the display for performing the one-touch and one-scan payment;

wherein the NFC is used to establish radio communication with the external device by touching the housing and the external device or bringing the housing and the external device into proximity, the proximity includes a distance of up to 10 centimeters;

wherein the processor is operable to operate in three modes, the three modes including an NFC target mode when the device is acting as a credential, a NFC initiator mode when the device is acting as a reader, and an NFC peer-to-peer mode;

wherein the payment is further associated with advertisement tags, two-dimensional barcodes, and ultra-high frequency tags;

wherein the processor is operable to be connected to a cloud;

wherein user credentials are provisioned over the air;

the payment being associated with a payment application associated with the processor to control transferring of the payment and access payment readers;

wherein the NFC unit is operable to connect to a third-party NFC device with a server for data;

wherein the device is adapted to enable a Bluetooth low energy payment;

wherein the device is associated with one or more of a transactional payment based on Unstructured Supplementary Service Data, Short Message Service, direct operator billing, a credit card mobile payment, an online wallet, a QR code payment, contactless NFC, a cloud-based mobile payment, an audio signal-based payment, a Bluetooth Low Energy signal beacon payment, an in-application payment, a Software Development Kit payment, an Application Programming Interface payment, a social networking payment, and a direct carrier and bank co-operation.

20. The device of claim 1, wherein the processor is further operable to:

detect current user location;

detect presence of premises associated with the user in proximity to the current user location; and based on the detecting, unlock the premises.

21. The device of claim 1, wherein the biometric sensors are operable to non-invasively monitor a glucose level, the glucose level being monitored using a saliva testing;

wherein the processor is associated with an operating system operable to pair with third-party applications running on the external device;

wherein the processor integrates a third-party developer technology and the third-party applications and notifications into a form factor;

wherein the processor is operable to download applications;

wherein the device acts as or is associated with smart textiles, an activity tracker, a smartwatch, smartglasses, a GPS watch, mixed reality, computer-mediated reality, clothing technology, Smart closing, healthcare, augmenter reality, and smart and connected devices.

22. The device of claim 1, wherein the processor is further operable to:

detect presence of another wearable personal digital device for facilitating mobile device payments, personal use, and health care in proximity to the wearable personal digital device for facilitating mobile device payments, personal use, and health care; and based on the detecting, initiate data transmission between the wearable personal digital device for facilitating mobile device payments, personal use, and health care and another wearable personal digital device for facilitating mobile device payments, personal use, and health care.

23. The device of claim 1, wherein the processor is further operable to:
receive, from the user, a content access request for at least one content item of content data stored in the memory unit;
reading access rules stored in the memory unit, the access rules being associated with a use of the at least one content item;
determine, based on the access rules, that an access to the at least one content item is permitted; and
reproduce, based on the determining, the at least one content item to the user; wherein the content data includes audio data, video data, text, software, game data; wherein the device acts as a data carrier and includes an interface for sending and receiving data, the memory unit being operable to store received content data, provide payment validation data to the external device, store a record of access made to the stored content data, and the access rules for controlling access to the stored content data; the processor being further operable to access control data and supplementary data including hot links to websites and advertising data; wherein payment data, the stored content data and access rules data are used to reduce a risk of an unauthorized access to the content data.

* * * * *